United States Patent [19]
Aldrich et al.

[11] Patent Number: 6,025,305
[45] Date of Patent: *Feb. 15, 2000

[54] PROCESS FOR PRODUCING A LUBRICANT BASE OIL HAVING IMPROVED OXIDATIVE STABILITY

[75] Inventors: Haven Scott Aldrich, Annandale; John Stephen Szobota, Morristown, both of N.J.; Robert Jay Wittenbrink, Baton Rouge, La.

[73] Assignee: Exxon Research and Engineering Co., Florham Park, N.J.

[ * ] Notice: This patent is subject to a terminal disclaimer.

[21] Appl. No.: 09/128,727

[22] Filed: Aug. 4, 1998

[51] Int. Cl.⁷ .................... C10M 109/00; C10M 101/02
[52] U.S. Cl. ............. 508/110; 250/339.08; 250/339.12; 585/253; 702/30
[58] Field of Search ................ 508/110; 250/339.08, 250/339.12; 585/253; 702/30

[56] References Cited

U.S. PATENT DOCUMENTS

| | | | |
|---|---|---|---|
| 4,832,819 | 5/1989 | Hamner | 208/27 |
| 4,943,672 | 7/1990 | Hamner et al. | 585/737 |
| 5,404,015 | 4/1995 | Chimenti et al. | 250/339.12 |
| 5,419,185 | 5/1995 | Chimenti et al. | 73/54.01 |
| 5,424,542 | 6/1995 | Chimenti et al. | 250/339.12 |
| 5,426,053 | 6/1995 | Chimenti et al. | 436/55 |
| 5,475,612 | 12/1995 | Espinosa et al. | 364/500 |

FOREIGN PATENT DOCUMENTS

WO 99/20720  4/1999  WIPO .......................... C10M 143/08

OTHER PUBLICATIONS

L.M. Petrova, et al., Composition and Properties of Lube Oil from Heavy Crudes Produced from Permian Deposits, Chemistry and Technology of Fuels and Oils, vol. 31, Nos 5–6 (1995) pp. 236–240, 1995.

K.I. Zimina, et al, "Methods of Comprehensive Investigation of the Composition, Structure and Properties of Oil Hydrocarbons", Scientific Papers of the Prague Institute of Chemical Technology, D 46 (1982), Technology of Fuel, pp. 89–103.

D. Christakudis, et al, "Several properties of Lubricating Oils Produced by Thermaldiffusion", Organic–Technical Chemistry, Chemistry Dept. at the Bergakademie at Freiberg and presented to the 10th International Symposium "Lubricants, Lubrication and Bearing Engineering" (Aug. 27–31, 1998), pp. 32–41.

G.E. Cranton, "Composition and Oxidation of Petroleum Fractions", Elsevier Scientific Publishing Company, Thermochimica Acta (1976), 14 (1–2), pp. 201–208.

G.E. Fodor, "An Analysis of Petroleum Fuels by Midband Infrared Spectroscopy", SAE International Congress (Detroit Feb. 28–Mar. 3, 1994), SAE Meeting Paper (1994), 14 pps.

S. Garrigues, et al, "Multivariate Calibrations in Fourier Transform Infrared Spectrometry for Prediction of Kerosene Properties", Analytical Chimica Acta 317 (1–3) (1995), pp. 95–105.

*Primary Examiner*—Jerry D. Johnson

[57] ABSTRACT

The instant invention is directed to a process for producing an improved lubricating base stock having a preselected desired oxidation stability comprising the steps of: (a) hydroisomerizing a hydrocarbon wax to obtain a lubricating base stock, (b) irradiating, within the frequency of about 4600 to about 3500 cm$^{-1}$ or about 1300 to about 600 cm$^{-1}$, said lubricating base stock produced from hydroisomerization of said hydrocarbon wax, (c) measuring the absorption spectrum, within said frequency range of step (b), of said lubricating base stock using FT-IR, (d) converting said absorption spectrum into a number representative of the viscosity index of said lubricating base stock of step (a), (e) comparing the viscosity index produced in step (c) to a preselected viscosity index correlating to a preselected desired oxidative stability for said lubricating base stock of step (a), and then, (f) modifying said hydroisomerization of said hydrocarbon wax to increase the production of lubricating base stock having said preselected desired oxidative stability of step (e).

9 Claims, No Drawings

PROCESS FOR PRODUCING A LUBRICANT BASE OIL HAVING IMPROVED OXIDATIVE STABILITY

FIELD OF THE INVENTION

The instant invention is directed to a process for the production of high quality lubricant base oils having superior oxidation stability using molecular structure control and FT-IR chemometric controls.

BACKGROUND OF THE INVENTION

Studies to date have shown that lubricants prepared via the hydro-isomerization of Fischer-Tropsch wax, are equivalent to synthetic lubricants, such as polyalphaolefins (PAO, oligomers of a-decene) in all areas of performance except low temperature performance and base oil oxidation stability. Therefore, a process is needed which is capable of increasing the oxidation stability of hydroisomerized Fischer-Tropsch waxes.

At present, the API "SH" rating is currently employed for passenger car motor oils for use in gasoline engines which represents a significant increase in the service requirements of lubricants from past ratings (e.g., API SF or API SG). Thus, there is a continuing need for lubricants with superior performance characteristics.

One of the performance characteristics which is of greatest significance is the viscosity index (VI). This represents the extent to which the viscosity of a lubricant varies with temperature. Lubricants of high VI change relatively little in viscosity as temperature increases, at least as compared to lubricants of lower VI. Since retention of viscosity at higher temperatures is a desirable characteristic, high viscosity index is desirable. Satisfactory viscosity properties may be conferred either by suitable choice of the lubricant base stock or by the use of VI improvers which are generally high molecular weight polymers.

The extent to which VI properties can be varied by the use of these improvers is, however, limited because not only are large amounts of improver expensive but the improvers are subject to degradation in use so that service life of lubricants containing large amounts of improver may be limited. This implies that improvements in the VI of the base stock are desirable. However, such improvers will have no affect on the oxidation stability of a base stock.

Spectroscopic methods have been used in the art. U.S. Pat. No. 5,475,612 is directed to determining the properties of a liquid hydrocarbon blend from the near IR spectrum of the components of the blend. The method involves determining the absorbance, at a minimum number of frequencies, for the components of arbitrary mixtures. A spectral mixture index is then determined for each component and property. The desired property sought is then calculated by a linear expression.

U.S. Pat. No. 5,419,185 is directed to a method and apparatus for optimizing the extraction of aromatics from waxy distillates and the dewaxing of waxy raffinates in the manufacture of lubricating oils. The method involves irradiating a waxy raffinate, measuring the absorption spectrum and converting the spectrum into a number representative of the VI of the dewaxed oil produced from the waxy raffinate after dewaxing. The aromatics extraction of a waxy distillate which produces the waxy raffinate is then reduced or increased in severity in order to approach a desired VI.

Other articles include "An analysis of petroleum fuels by midband (4000-400/cm) infrared spectroscopy", Foder G. E. et al., SAE International Congress(Detroit 2/28-3/3/94) SAE Meeting Paper N 941019(1994)14P, ISSN 0148-7191 and "Multivariate Calibration in Fourier Transform Infrared Spectrometry for Prediction of Kerosene Properties", Garrigues S. et al., Anal. Chim. Acta., 317(1–3)95–105(1995) Chemical Abstracts ABSTR No. 92150 V124 N. 8 ISSN 0009-2258.

Several articles have been written on thermal diffusion of particular materials such as residual lube stocks (The Composition and Properties of Oil Fractions in Heavy Crudes from the Persian Deposits of Tartarstan, Petrova et al., Russian Academy of Sciences, Kazan Branch, Institute of Organic & Physical Chemistry, Khimiya i Tekhnologiya Topliv I Masel N.5 33–35 (1995) ISSN 0023–1169); MS-8 Oils (Oxidation Tendency of Fractions from the thermal diffusion separation of white oil, Klimov, A.K. et al., Neftepererab. Neftekhim (Moscow) (1979), (1), 23-5 CODEN:NNNSAF; ISSN 0028–1190: Deparaffinated heavy oil, refined neutral II and hydrofined neutral III (Properties of Lubricating oils produced by thermal diffusion, Christakudis et al., Schmierstoffe Schmierungstech. (1969), No. 35, 32–41, CODEN:SSWTBI; and petroleum lube oils (Composition and oxidation of petroleum fractions, Cranton, G. E., Thermochim Acta (1976), 14(1–2), 201-8 CODEN:THACAS.

SUMMARY OF THE INVENTION

The instant invention is directed to a process for producing a lubricating base stock having a preselected desired oxidation stability comprising the steps of:

(a) hydroisomerizing a hydrocarbon wax to obtain a lubricating base stock, (b) irradiating, within the frequency of about 4600 to about 3500 $cm^{-1}$ or about 1300 to about 600 $cm^{-1}$, said lubricating base stock produced from hydroisomerization of said hydrocarbon wax, (c) measuring the absorption spectrum, within said frequency range of step (b), of said lubricating base stock using FT-IR, (d) converting said absorption spectrum into a number representative of the viscosity index of said lubricating base stock of step (a), (e) comparing the viscosity index produced in step (c) to a preselected viscosity index correlating to a preselected desired oxidative stability for said lubricating base stock of step (a), and then, (f) modifying said hydroisomerization of said hydrocarbon wax to increase the production of lubricating base stock having said preselected desired oxidative stability of step (e).

DETAILED DESCRIPTION OF THE INVENTION

Applicants have discovered that there exists a particular branchy hydrocarbon mixture having a degree of branchiness which confers highly improved oxidative stability to a hydroconverted hydrocarbonaceous feed stock. A highly improved product can be obtained from a fractionated hydroisomerized hydrocarbon feed, for example, a hydroisomerized Fischer-Tropsch wax.

The instant invention describes a process for improving the oxidation stability of lubricant base oils produced from hydroisomerized hydrocarbon waxes. The base oils are preferably derived from a synthetic wax produced using a Fischer-Tropsch (FT) process from a methane derived syngas.

Applicants have observed that a particular fraction of the 700° F.+ fraction of a hydroisomerized FT wax having a defined degree of branchiness is more oxidatively stable than components of higher and lower degrees of branchiness. Combining this finding with FT-IR and chemometrics, then allows the skilled artisan to control the isomerization to increase the yield of component having the most beneficial oxidative stability.

All that is necessary to carry out the process of the instant invention is that a target or desired viscosity index be known. This is the preselected VI of the instant invention. The target or desired VI can be determined by any means known to the skilled artisan. The target or desired VI will preferably be correlated with a target or desired oxidative stability by methods known to the skilled artisan. This target or desired oxidative stability is the preselected oxidative stability of the instant invention. Once a target VI correlating to a target oxidative stability is known, the process is conducted.

Applicants separated the 700° F.+ fraction of a hydroisomerized FT wax using thermal diffusion separation technique which separate hydrocarbons as a function of structure or molecular shape. Consequently, a mixture of hydrocarbons that range from normal paraffins to highly branched paraffins are separated such that the normal paraffins are eluded first while the most highly branched are eluded last. Branchiness increases as one proceeds to higher ports. One skilled in the art would expect that the least highly branched paraffins, those with the highest VI, would show the greatest oxidation stability. Hence, the least highly branched paraffins would be selected for use as base stocks. Applicants have found that this is not the case. Applicants believe that a particular level, or mixture of branchiness, can retard the level of oxidation by interfering with the ability of hydroperoxides to react with other reactive hydrogens through stearic blocking. Therefore, the random branchiness which result in tertiary hydrogens more reactive in an oxidation environment is being counterbalanced. This is unexpected and previously unknown. Though thermal diffusion was used to separate the fractions of the hydroisomerized wax, any method of separation based on molecular shape can be utilized.

By measuring the VI and oxidative stability, using known techniques, of each of the fractions produced by the thermal diffusion, applicants were able to identify a fraction comprising at least 50% of a mixture of branched paraffins, wherein said paraffins are paraffins having a carbon chain length of about $C_{20}$ to about $C_{40}$, having a molecular weight ranging from about 280 to about 562, and a boiling range of about 650° F. to about 1050° F., and wherein said branched paraffins contain up to 4 methyl branches, and wherein the free carbon index of said branched paraffins is at least about 3. This particular fraction has a higher oxidative stability than the other fractions separated. The fraction will also preferably have a number of pendant carbon of about 4 or less. The number of pendant carbon is defined as the number of alkyl groups on the $\epsilon(+)$ carbons. Thus pendent carbons will be present in the middle of the carbon chain at least $\epsilon(+)$ carbons from each end of the chain. Knowing the VI of this material, applicants are then able to utilize FT-IR and chemometrics to measure the VI of the stream produced from the hydroisomerization of a Fischer-Tropsch wax, compare this measured VI to the target or desired VI, corresponding to the above fraction, and modify the hydroisomerization process to increase the concentration of the branched paraffin mixture corresponding to the target VI and hence the desired oxidation stability. Thus, modification of the molecular structure of wax isomerate produced from the hydrocarbon wax, by modifying the hydro-isomerization, allows the skilled artisan to produce a product of target VI and oxidative stability. Though applicants were comparing the VI of the hydro-isomerized wax to the fraction having the above characteristics, the instant method can be utilized to increase the concentration of product having any given VI. All that is necessary is that a desired or target VI be available for comparison. The desired or target VI may correspond to any oxidative stability being sought. Preferably, the VI will correspond to an improved oxidative stability.

The base stock applicants sought to produced has a "Free Carbon Index" (or FCI) of at least about 3. The term "Free Carbon Index" is a measure of the number of carbons in an iso-paraffin that are located at least 4 carbons from a terminal carbon and more than 3 carbons away from a side chain. The FCI of an isoparaffin can be determined by measuring the percent of methylene groups in an isoparaffin sample using $^{13}$C NMR (400 megahertz); multiplying the resultant percentages by the calculated average carbon number of the sample determined by ASTM Test method 2502 and dividing by 100.

The FCI is further explained as follows. The base stock is analyzed by $^{13}$C NMR using a 400 MHz spectrometer. All normal paraffins with carbon numbers greater than $C_9$ have only five non-equivalent NMR adsorptions corresponding to the terminal methyl carbons ($\alpha$) methylenes from the second, third and forth positions from the molecular ends ($\beta$, $\gamma$, and $\delta$ respectively), and the other carbon atoms along the backbone which have a common chemical shift (s). The intensities of the $\alpha$, $\beta$, $\gamma$ and $\delta$ are equal and the intensity of the $\epsilon$ depends on the length of the molecule. Similarly the side branches on the backbone of an iso-paraffin have unique chemical shifts and the presence of a side chain causes a unique shift at the tertiary carbon (branch point) on the backbone to which it is anchored. Further, it also perturbs the chemical sites within three carbons from this branch point imparting unique chemical shifts ($\alpha'$, $\beta'$ and $\gamma'$).

The Free Carbon Index (FCI) is then the percent of $\epsilon$ methylenes measured from the overall carbon species in the $^{13}$C NMR spectra of the base stock, divided by the average carbon number of the base stock as calculated from ASTM method 2505, divided by 100.

If desirable, the skilled artisan could determine which fractions have equivalent VI and oxidative stability of a given PAO oil, run the process and prepare a lubricating oil from a Fischer-Tropsch wax which could be substituted for the given PAO. The prepared oil would then behave equivalently in all areas of performance including base oil oxidative stability.

Though the above discussion and the discussion to follow is in the context of Fischer-Tropsch waxes, those skilled in the art can readily see that the instant process can be compared to any wax hydroisomerization processes. All that is necessary is that a desired VI be known or determined.

The hydroisomerized waxes utilizable in the instant invention may originate from any number of sources including petroleum raffinates. Synthetic waxes from Fischer-Tropsch processes may be used, as may be waxes recovered from the solvent or autorefrigerative dewaxing of conventional hydrocarbon oils, or mixtures of these waxes. Waxes from dewaxing conventional hydrocarbon oils, commonly called slack waxes may also be used.

Though the waxes can be hydroisomerized by conventional prior art methods, typically the hydroisomerization is conducted over a catalyst containing a hydrogenating metal component-typically one from Group IV, or Group VIII of the Periodic Table, or mixtures thereof. The reaction is conducted under conditions of temperature between about 500 to 750° F. (preferably 570 to 680° F.) and pressures of from 500 to 3000 psi $H_2$ (preferably 500–1500 psi $H_2$), at hydrogen gas rates from 1000 to 10,000 SCF/bbl, and at space velocities in the range of from 0.1 to 10 v/v/hr, preferably from 0.5 to 2 v/v/hr.

Following the hydroisomerization, the isomerate may undergo hydrogenation to stabilize the oil and remove residual aromatics. The resulting product may then be fractionated into lubricants and fuels. Typically, the initial boiling point of the lubricants fraction will boil in the range of about 650° F. to 700° F. or higher. It is the lubricant fraction that is utilized in the instant invention and which is irradiated. For Fischer-Tropsch waxes, the 700° F.+ fraction will typically be used.

The chemometric techniques utilized herein are known to the skilled artisan and are merely mathematical manipulations for converting an absorption spectrum into a number representative of VI. For example Multivariate Partial Least Squares (PLS), Multivariate Principal Component Regression (PCR), first derivative without baseline correction, mean centering, etc., can be used. PLS and PCR are preferred.

Though thermal diffusion was utilized to separate the hydro-isomerized wax into fractions, any technique known to the skilled artisan which separates based on molecular structure can be utilized.

The method for monitoring the thermal diffusion fractions for oxidation stability can be any method known to those skilled in the art. For example, measurement of the oxidation induction time using high pressure differential scanning calorimetry can be used. Likewise, NMR techniques can be used to determine the molecular structure of the fractions.

Once it is determined which cuts of the thermally diffused feed stream have the most beneficial oxidation stability or any desired oxidation stability, the corresponding VI's are then determined. It is then possible to utilize FT-IR techniques to accurately measure the VI of these particular cuts and then to predict corresponding oxidation stability such cuts will have. Utilizing this information, it then becomes possible to monitor, on-line or at line, the hydro-isomerization process producing the Fischer-Tropsch feed stream, alter the process conditions to obtain the FT-IR spectra of the most beneficial cuts, and thereby selectively produce lubricants with enhanced oxidation stability. It is within the skill in the art to modify the process conditions to obtain the FT-IR spectra corresponding to the product desired.

The wavelength range for irradiation of the isomerate can be performed in one of two regions. The first region is about 4600 to about 3500, preferably about 4600 to about 3950, and the second region is about 1300 to about 600, preferably about 850 to about 650 $cm^{-1}$. Preferably a combination of the two wavelength regions will be utilized.

The following examples are merely for illustration and are not meant to be limiting in any way.

Example 1

A sample of Fischer-Tropsch wax was subjected to hydroisomerization under hydroconversion conditions which were sufficient enough to cause ≅50% conversion of the 700° F.+ wax into high quality liquid transportation fuels boiling below 700° F. The resulting 700° F.+ hydroisomerate was then fractionated into a 700–950° F. fraction. This fraction was then separated into 10 cuts using thermal diffusion (P1–P10). The feedstock and the cuts were evaluated to measure their oxidation stabilities using High Pressure Differential Scanning Calorimetry (HPDSC). Each sample was blended with a constant amount of dioctyldiphenyl amine antioxidant. The concentration of antioxidant was 0.5 wt % on the base oil in each case. The samples were evaluated in open aluminum pans under 200 psi of $O_2$ at constant temperature and the stability was measured by the oxidation induction time (OIT) in minutes. The longer the OIT for a cut at a fixed temperature, the more stable is that lubricant thermal diffusion cut. Each thermal diffusion cut was evaluated at 170, 180, and 190° C. The relative stability is determined by comparing OITs at a fixed temperature. The stability of the cuts was not equal and showed an increase between ports 2 and 6 followed by a steady decrease after that.

The results are shown in Table I.

TABLE I

| Port Number | HPDSC Isothermal Temperature, ° C. | Oxidation Induction Time (Minutes) |
|---|---|---|
| 1 | 170 | 21.0 |
| 1 | 180 | 14.4 |
| 1 | 190 | 5.8 |
| 2 | 170 | 32.4 |
| 2 | 180 | 14.8 |
| 2 | 190 | 8.5 |
| 3 | 170 | 25.2 |
| 3 | 180 | 15.1 |
| 3 | 190 | 17.6 |
| 4 | 170 | 37.4 |
| 4 | 180 | 20.7 |
| 4 | 190 | 9.9 |
| 5 | 170 | 34.6 |
| 5 | 180 | 19.0 |
| 5 | 190 | 9.5 |
| 6 | 170 | 32.8 |
| 6 | 180 | 16.0 |
| 6 | 190 | 7.6 |
| 7 | 170 | 25.1 |
| 7 | 180 | 13.3 |
| 7 | 190 | 6.4 |
| 8 | 170 | 16.4 |
| 8 | 180 | 10.1 |
| 8 | 190 | 5.8 |
| 9 | 170 | 15.6 |
| 9 | 180 | 10.0 |
| 9 | 190 | 5.9 |
| 10 | 170 | 15.3 |
| 10 | 180 | 10.5 |
| 10 | 190 | 6.9 |

FT-IR spectra recorded for 6 of the thermal diffusion cuts encompassing passing the range of viscosity and viscosity index values (P1, P3, P5, P7, P9, and P10, P=Port) can be used to predict the viscosity and viscosity indices. Spectra were recorded using a 1.0 mm path length standard liquid IR cell fitted with KBr windows. Spectra were obtained at 2 $cm^{-1}$ resolution utilizing 100 scans for both sample and background. A Multivariate Partial-Least Squares Chemometric methodology was used to generate a calibration capable of predicting viscosity and viscosity index to a high degree of accuracy. The spectral regions found to provide the best fit for this analysis were from 4600 to 3950 $cm^{-1}$ and 850 to 650 $cm^{-1}$. These regions exhibit features due to both methylene and methyl groups, consistent with degree of branchiness being an important factor.

Tables II through IV show the viscosity at 40 and 100° C., viscosity index, number of chemometric factors used and correlation coefficients and root mean square deviation (RMSD) for two different predictions of viscosity and VI-self prediction, i.e., sample predicted was part of calibration set, and Leave-one-out Prediction, i.e., sample predicted was not included in calibration set (this is considered to give a better measure of model prediction capability for real unknown samples).

TABLE II

FT-IR PREDICTIONS OF VISCOSITY AT 40° C.
3 FACTORS USED

| Sample Port Number | Actual Viscosity | Self Prediction Viscosity | Leave-one-out Prediction Viscosity |
|---|---|---|---|
| 1 | 23.91 | 23.969 | 24.024 |
| 3 | 27023 | 27.047 | 26.988 |
| 5 | 28.75 | 28.809 | 28.830 |
| 7 | 30.44 | 30.508 | 30.753 |
| 9 | 32.62 | 32.743 | 32.882 |
| 10 | 33.94 | 33.812 | 32.320 |
| RMSD | | 0.11305 | 0.32736 |
| Correlation Coefficient | | 0.99886 | 0.99044 |

TABLE III

FT-IR CHEMOMETRIC PREDICTIONS OF VISCOSITY AT
100° C. 3 FACTORS USED

| Sample Port Number | Actual Viscosity | Self Prediction Viscosity | Leave-one-out Prediction Viscosity |
|---|---|---|---|
| 1 | 5.20 | 5.203 | 5.153 |
| 3 | 5.48 | 5.470 | 5.476 |
| 5 | 5.63 | 5.631 | 5.598 |
| 7 | 5.79 | 5.803 | 5.836 |
| 9 | 6.04 | 6.030 | 6.019 |
| 10 | 6.12 | 6.123 | 6.107 |
| RMSD | | 0.0081523 | 0.0316 |
| Correlation Coefficient | | 0.99933 | 0.99005 |

TABLE IV

FT-IR CHEMOMETRIC PREDICTIONS OF VISCOSITY INDEX
1 FACTOR USED

| Sample Port Number | Actual Viscosity | Self Prediction Viscosity | Leave-one-out Prediction Viscosity |
|---|---|---|---|
| 1 | 156 | 155.19 | 153.16 |
| 3 | 143 | 144.36 | 144.76 |
| 5 | 140 | 140.25 | 140.30 |
| 7 | 135 | 135.11 | 135.14 |
| 9 | 133 | 130.74 | 129.70 |
| 10 | 128 | 129.32 | 130.10 |
| RMSD | | 1.2519 | 2.1041 |
| Correlation Coefficient | | 0.98036 | 0.94452 |

Because the viscosities and VI of the thermal diffusion cuts can be predicted based on FT-IR data, the oxidation stabilities can also be predicted as both are a function of the branchiness of the 700 F+ LUBE-X fraction. In manufacturing operations, in which the temperature and space velocity of feed over catalyst are controllable, FT-IR can be used as an on line or at-line analytic to maximize the content of the feed stream that has the spectral properties corrsponding to the branchiness that is responsible for the superior oxidation stability.

The following tables show the viscosity at 40° C., 100° C., viscosity index number of chemometric factors used and correlation coefficients and RMSD for two different predictions of viscosity and VI-self prediction ( i.e., the sample predicted was part of the calibration set) and leave-one-out prediction (i.e., the sample predicted was not included in the calibration set (considered to give a better measure of model prediction capability for real unknown examples).

Multivariate chemometric methodologies [partial least squares and principal component regression] were utilized to generate a calibration capable of predicting viscosity and viscosity index to a high degree of accuracy. Various region of the spectrum which exhibit features due to both methylene and methyl groups were utilized. Pre-processing included mean centering and baseline correction. Tabulated below are self-prediction (i.e., sample predicted was part of the calibration set) and correlation coefficient ($r^2$) obtained.

| Predicted Property | Multivariate methodology # of Factors | PLS Correlation Coefficient ($r^2$) |
|---|---|---|
| Spectral Region 4600–3510 cm$^{-1}$ | | |
| Viscosity @ 40° C. | 1 | 0.953 |
| Viscosity @ 100° C. | 1 | 0.937 |
| Viscosity Index | 1 | 0.970 |
| Spectral Region 4600–3900 cm$^{-1}$ | | |
| Viscosity @ 40° C. | 1 | 0.953 |
| Viscosity @ 100° C. | 1 | 0.934 |
| Viscosity Index | 2 | 0.963 |
| Spectral Region 1300–600 cm$^{-4}$ | | |
| Viscosity @ 40° C. | 4 | 0.953 |
| Viscosity @ 100° C. | 3 | 0.993 |
| Viscosity Index | 1 | 0.947 |
| Spectral Region 850–600 cm$^{-1}$ | | |
| Viscosity @ 40° C. | 3 | 0.965 |
| Viscosity @ 100° C. | 3 | 0.988 |
| Viscosity Index | 1 | 0.949 |
| Spectral Region 1200–850 cm$^{-4}$ | | |
| Viscosity @ 40° C. | 4 | 0.986 |
| Viscosity @ 100° C. | 2 | 0.984 |
| Viscosity Index | 1 | 0.940 |
| Spectral Region 1000–850 cm$^{-1}$ | | |
| Viscosity @ 40° C. | 3 | 0.960 |
| Viscosity @ 100° C. | 3 | 0.967 |
| Viscosity Index | 2 | 0.946 |
| Spectral Region 1360–650 cm$^{-1}$ | | |
| Viscosity @ 40° C. | 2 | 0.977 |
| Viscosity @ 100° C. | 3 | 0.978 |
| Viscosity Index | 1 | 0.925 |
| Spectral Region 4600–3510 cm$^{-1}$ | | |
| Viscosity @ 40° C. | 3 | 0.923 |
| Viscosity @ 100° C. | 3 | 0.916 |
| Viscosity Index | 3 | 0.962 |
| Spectral Region 4600–3900 cm$^{-1}$ | | |
| Viscosity @ 40° C. | 2 | 0.935 |
| Viscosity @ 100° C. | 2 | 0.916 |
| Viscosity Index | 2 | 0.962 |
| Spectral Region 1300–600 cm$^{-1}$ | | |
| Viscosity @ 40° C. | 1 | 0.945 |

-continued

| Predicted Property | Multivariate methodology # of Factors | PLS Correlation Coefficient ($r^2$) |
|---|---|---|
| Viscosity @ 100° C. | 1 | 0.921 |
| Viscosity Index | 1 | 0.947 |
| Spectral Region 850–650 cm$^{-1}$ | | |
| Viscosity @ 40° C. | 1 | 0.942 |
| Viscosity @ 100° C. | 1 | 0.917 |
| Viscosity Index | 1 | 0.949 |
| Spectral Region 1200–350 cm$^{-1}$ | | |
| Viscosity @ 40° C. | 1 | 0.945 |
| Viscosity @ 100° C. | 1 | 0.923 |
| Viscosity Index | 1 | 0.940 |
| Spectral Region 1000–850 cm$^{-1}$ | | |
| Viscosity @ 40° C. | 2 | 0.952 |
| Viscosity @ 100° C. | 2 | 0.954 |
| Viscosity Index | 2 | 0.943 |
| Spectral Region 1360–650 cm$^{-1}$ | | |
| Viscosity @ 40° C. | 1 | 0.972 |
| Viscosity @ 100° C. | 1 | 0.957 |
| Viscosity Index | 1 | 0.925 |

Utilization of other subregions within the 4600-3510 cm$^{-1}$ give rise to correlation coefficients of similar magnitude. Baseline correction gave better correlation coefficients than utilization of mean centering and 1st derivative (without baseline correction) pre-processing.

Utilization of combination of two regions (one from 4600-3510 cm$^{-1}$ and the other from the 1360-650 cm$^{-1}$ region gave rise to significantly improved correlation as shown below.

| Spectral Region 4600–3950 cm$^{-1}$ and 850–650 cm$^{-1}$ Predicted Property | Multivariate methodology # of Factors | PLS Correlation Coefficient ($r^2$) |
|---|---|---|
| Viscosity @ 40° C. | 3 | 0.999 |
| Viscosity @ 100° C. | 3 | 0.999 |
| Viscosity Index | 1 | 0.980 |

What is claimed is:

1. A process for producing a lubricating base stock having a desired oxidation stability comprising the steps of
   (a) hydroisomerizing a hydrocarbon wax to obtain a lubricating base stock,
   (b) irradiating, within the frequency of about 4600 to about 3500 cm$^{-1}$ or about 1300 to about 600 cm$^{-1}$, said lubricating base stock produced from hydroisomerization of said hydrocarbon wax,
   (c) measuring the absorption spectrum, within said frequency range of step (b), of said lubricating base stock using FT-IR,
   (d) converting said absorption spectrum into a number representative of the viscosity index of said lubricating base stock of step (a),
   (e) comparing the viscosity index produced in step (d) to a viscosity index correlating to a preselected desired oxidative stability for said lubricating base stock of step (a), and then,
   (f) modifying said hydroisomerization of said hydrocarbon wax to increase the production of lubricating base stock having said desired oxidative stability of step (e).

2. The process of claim 1 wherein said hydrocarbon wax is a Fischer-Tropsch wax.

3. The process of claim 1 wherein when said wax is a Fischer-Tropsch wax, the lubricating base stock having the desired viscosity index correlating to the preselected oxidative stability of step (e) is a mixture of branched paraffins, wherein said paraffins are paraffins having a carbon chain length of about $C_{20}$ to about $C_{40}$, having a molecular weight ranging from about 280 to about 562, and a boiling range of about 650° F. to about 1050° F., and wherein said branched paraffins contain up to 4 methyl branches, and wherein the free carbon index of said branched paraffins is at least about 3.

4. The process of claim 1 wherein said hydrocarbon wax is selected from the group consisting of petroleum raffinates, slack waxes, Fischer-Tropsch waxes and mixtures thereof.

5. The process of claim 1 wherein said viscosity index correlating to a desired oxidative stability is determined by separating, based on molecular structure, said hydroisomerized hydrocarbon wax of step (a) into a plurality of fractions and determining the viscosity index and corresponding oxidative stability of each of said separated fractions to identify the fractions having a desired viscosity index and oxidative stability.

6. The process of claim 5 wherein said separation of said hydroisomerized wax is conducted using thermal diffusion.

7. The process of claim 1 wherein a combination of said wavelengths of step (b) is utilized.

8. The process of claim 3 wherein said mixture of branched paraffins comprises paraffins having an average number of pendant carbons of 4 or less.

9. The process of claim 5 wherein said desired oxidative stability is the highest oxidative stability.

* * * * *